US011965848B2

(12) United States Patent
Godbole et al.

(10) Patent No.: US 11,965,848 B2
(45) Date of Patent: Apr. 23, 2024

(54) METHOD FOR DETERMINING THE ELECTRICAL PROPERTIES OF A CORE SAMPLE

(71) Applicant: SAUDI ARABIAN OIL COMPANY, Dhahran (SA)

(72) Inventors: Atul Godbole, Dhahran (SA); Sultan Muhammad Al Enezi, Dammam (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 209 days.

(21) Appl. No.: 17/457,499

(22) Filed: Dec. 3, 2021

(65) Prior Publication Data

US 2023/0175998 A1  Jun. 8, 2023

(51) Int. Cl.
*G01N 27/12* (2006.01)
*G01N 1/34* (2006.01)
*G01N 33/24* (2006.01)

(52) U.S. Cl.
CPC .............. *G01N 27/12* (2013.01); *G01N 1/34* (2013.01); *G01N 33/24* (2013.01)

(58) Field of Classification Search
CPC .......... G01N 27/12; G01N 1/34; G01N 33/24; G01N 15/08; G01N 27/041
(Continued)

(56) References Cited

U.S. PATENT DOCUMENTS 4,907,448 A   3/1990 Givens
4,924,187 A   5/1990 Sprunt et al.
(Continued)

FOREIGN PATENT DOCUMENTS

CN   102243196 B   7/2012
CN   102565858 B   4/2014
CN   105240003 A   1/2016

OTHER PUBLICATIONS

Anderson, William G., "Wettability Literature Survey-Part 3: The Effects of Wettability on the Electrical Properties of Porous Media", Journal of Petroleum Technology, pp. 1371-1378, Dec. 1986 (8 pages).
(Continued)

*Primary Examiner* — Giovanni Astacio-Oquendo
(74) *Attorney, Agent, or Firm* — Osha Bergman Watanabe & Burton LLP

(57) ABSTRACT

A method for determining the electrical properties of a core sample having an initial saturation $S_{w0}$, an initial true resistivity $R_{t0}$, and a porosity $\phi$, including the steps: preparing a brine having a resistivity $R_w$, flushing the core sample with the brine, determining a first true resistivity $R_{t1}$ at a first saturation $S_{w1}$, once the resistivity $R_w$ of the brine going into the core sample is the same as the resistivity $R_w$ of the brine going out of the core sample, determining a function $R_t=f(S_w)$ describing the dependency of the true resistivity $R_t$ of the core sample and the saturation $S_w$ in the core sample, based on the initial saturation $S_{w0}$, initial true resistivity $R_{t0}$, first true resistivity $R_{t1}$, and first saturation $S_{w1}$, second true resistivity $R_{t2}$, and first saturation $S_{w2}$, determining the resistivity $R_o$ of the fully saturated core sample by estimating the function $R_t=f(S_w)$ to full saturation of the core sample at $S_w=100\%$, determining a resistivity index $$I_R = \frac{R_t}{R_o}$$

at the $S_w$, $S_{w1}$, $S_{w2}$ determining a saturation exponent n using linear regression of the log-log plot of $I_R$ vs. $S_w$.

20 Claims, 6 Drawing Sheets

(58) Field of Classification Search
USPC .............................. 324/693, 691, 649, 600
See application file for complete search history.

(56) References Cited

U.S. PATENT DOCUMENTS

| | | | |
|---|---|---|---|
| 4,926,128 | A | 5/1990 | Givens |
| 5,105,154 | A | 4/1992 | Givens et al. |
| 5,164,672 | A | 11/1992 | Gilliland et al. |
| 5,209,104 | A | 5/1993 | Collins et al. |
| 5,679,885 | A | 10/1997 | Lenormand et al. |
| 9,835,762 | B2 | 12/2017 | Pairoys |
| 10,451,763 | B2* | 10/2019 | Seleznev .............. G01N 15/088 |
| 10,816,494 | B2 | 10/2020 | Cerepi et al. |
| 2014/0318232 | A1 | 10/2014 | Pairoys |
| 2018/0010991 | A1* | 1/2018 | Rohan, Sr. ........... G01N 33/241 |
| 2018/0120468 | A1* | 5/2018 | Seleznev ................. G01V 3/20 |
| 2019/0369286 | A1* | 12/2019 | He .......................... G01V 3/38 |
| 2023/0008054 | A1* | 1/2023 | Gao ..................... G01N 24/081 |
| 2023/0045547 | A1* | 2/2023 | Nicot ................. G01N 15/0893 |

OTHER PUBLICATIONS

Sharma, Mukul M., et al., "Effects of Wettability, Pore Geometry, and Stress on Electrical Conduction in Fluid-Saturated Rocks", The Log Analyst, pp. 511-526, Sep.-Oct. 1991 (16 pages).

Gant, Preston L., et al., "Core Cleaning for Restoration of Native Wettability", SPE Formation Evaluaton, pp. 131-138, Mar. 1988 (8 pages).

Lasswell, Patrick M., "Core Analysis for Electrical Properties", Petrophysics, vol. 47, No. 3, pp. 191-213, Jun. 2006 (23 pages).

Newsham, Kent, et al., "As-Received Core Electrical Properties Tests for Determining Formation Factor FF and Resistivity Index RI", SPE-191476-MS, Society of Petroleum Engineers, pp. 1-18, 2018 (18 pages).

Wel, Jun-Zhl, et al., "Influence of Wettability on Two- and Four-Electrode Resistivity Measurements on Berea Sandstone Plugs", SPE Formation Evaluation, pp. 470-476, Dec. 1991 (7 pages).

* cited by examiner

METHOD FOR DETERMINING THE ELECTRICAL PROPERTIES OF A CORE SAMPLE

BACKGROUND

A petroleum reservoir, also called reservoir rock, contains oil and gas in porous or fractured rock reservoirs. To extract the oil and gas, wellbores are drilled into the reservoir rock.

Evaluating the potential of an oilfield reservoir requires evaluation of the properties of the oilfield reservoir. The properties of the oilfield reservoir comprise electrical conductivity (or resistivity), capillary pressure, water-flood behavior, relative permeability, dispersion, tertiary recovery, irreducible water saturation, and residual oil saturation of the reservoir. The potential of the oilfield reservoir is of special importance during the exploration phase of the oilfield reservoir. To predict the properties of a reservoir rock, a core sample is drilled out of the reservoir rock. However, the static and dynamic properties of the core sample change with its wettability.

A relationship between the electrical conductivity $C_t$ of the fluid saturated core sample, the electrical conductivity $C_w$ of the fluid, the porosity $\phi$ of the core sample, and the fluid saturation $S_w$ of the core sample with the fluid is described by Archie's law $$C_t = \frac{1}{a} C_w \phi^m S_w^n,$$

wherein m is the cementation exponent, n is the saturation exponent, and a is the tortuosity factor of the core sample. The cementation and saturation exponent m, n are important for calibrating logs, determining the porosity, and estimating the formation saturation values.

Conventional methods in the art take anywhere between 4-6 weeks from the time the core sample is received in the lab until the cementation and saturation exponents m, n are determined.

Accordingly, there exists a need for a fast method for determining the cementation and saturation exponent m, n of native state core samples that are freshly drilled out of the reservoir rock.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a method for determining the electrical properties of a core sample having an initial saturation $S_{w0}$, an initial true resistivity $R_{t0}$, and a porosity $\phi$, comprising the steps: preparing a brine having a resistivity $R_w$, flushing the core sample with the brine, determining a first true resistivity $R_{t1}$ at a first saturation $S_{w1}$, once the resistivity $R_w$ of the brine going into the core sample is the same as the resistivity $R_w$ of the brine going out of the core sample, determining a function $R_t = f(S_w)$ describing the dependency of the true resistivity $R_t$ of the core sample and the saturation $S_w$ in the core sample, based on the initial saturation $S_{w0}$, initial true resistivity $R_{t0}$, first true resistivity $R_{t1}$, and first saturation $S_{w1}$, second true resistivity $R_{t2}$, and first saturation $S_{w2}$, determining the resistivity $R_0$ of the fully saturated core sample by estimating the function $R_t = f(S_w)$ to full saturation of the core sample at $S_w = 100\%$, determining a resistivity index $$I_R = \frac{R_t}{R_o}$$

at the $S_{w0}$, $S_{w1}$ and $S_{w2}$, determining a saturation exponent n using linear regression of the log-log plot of $I_R$ vs. $S_w$.

Hence even before the wellbore is completed, the core sample makes the data for calibrating the electrical logs available. These values can also be compared with the electrical properties data on the same core samples after cleaning to understand the effect of wettability.

Other aspects and advantages of the claimed subject matter will be apparent from the following description and the appended claims.

DETAILED DESCRIPTION

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

Embodiments disclosed herein relate to a procedure for determining saturation exponent of native (fresh) state core samples and a method for estimating the Cementation Exponent (m). Both these values are important in calibrating logs and determining the porosity as well as estimating the formation saturation values.

More specifically, embodiments disclosed herein relate to a method for determining the electrical properties of a core sample having an initial saturation $S_{w0}$, an initial true resistivity $R_{t0}$, and a porosity $\phi$, comprising of the steps:

preparing a brine having a resistivity $R_w$, flushing the core sample with the brine, determining a first true resistivity $R_{t0}$ at a first saturation $S_{w0}$, once the resistivity $R_w$ of the brine going into the core sample is the same as the resistivity $R_w$ of the brine going out of the core sample, reversing the brine flow, allowing oil and gas to flow out and determining a first resistivity $R_{t1}$ at a first saturation $S_{w1}$ and second resistivity $R_{t2}$ at a second saturation $S_{w2}$, determining a linear function $R_t=f(S_w)$ describing the dependency of the true resistivity $R_t$ of the core sample and the saturation $S_w$ in the core sample, based on the initial saturation $S_{w0}$, initial true resistivity $R_{t0}$, first true resistivity $R_{t1}$, and first saturation $S_{w1}$, determining the resistivity $R_o$ of the fully saturated core sample by extrapolating the function $R_t=f(S_w)$ to full saturation of the core sample at $S_w=100\%$, determining a first true resistivity index $$I_{R0} = \frac{R_{t0}}{R_o}$$

at the first saturation $S_{w0}$, and subsequently a second and third resistivity index value using the same equation.

determining a linear function $R_t=f(S_w)$ and determining a saturation exponent $$n = -\frac{\log(I_R)}{\log(S_w)}.$$

In one or more embodiments, a cylindrical core sample is drilled horizontally out of the reservoir rock to be analyzed. In one or more embodiments, the core sample is up to 3.25 inch long (for a 4 inch core) which gives the core sample sufficient length and pore volume to increase the accuracy of the measurements.

Figure 1:
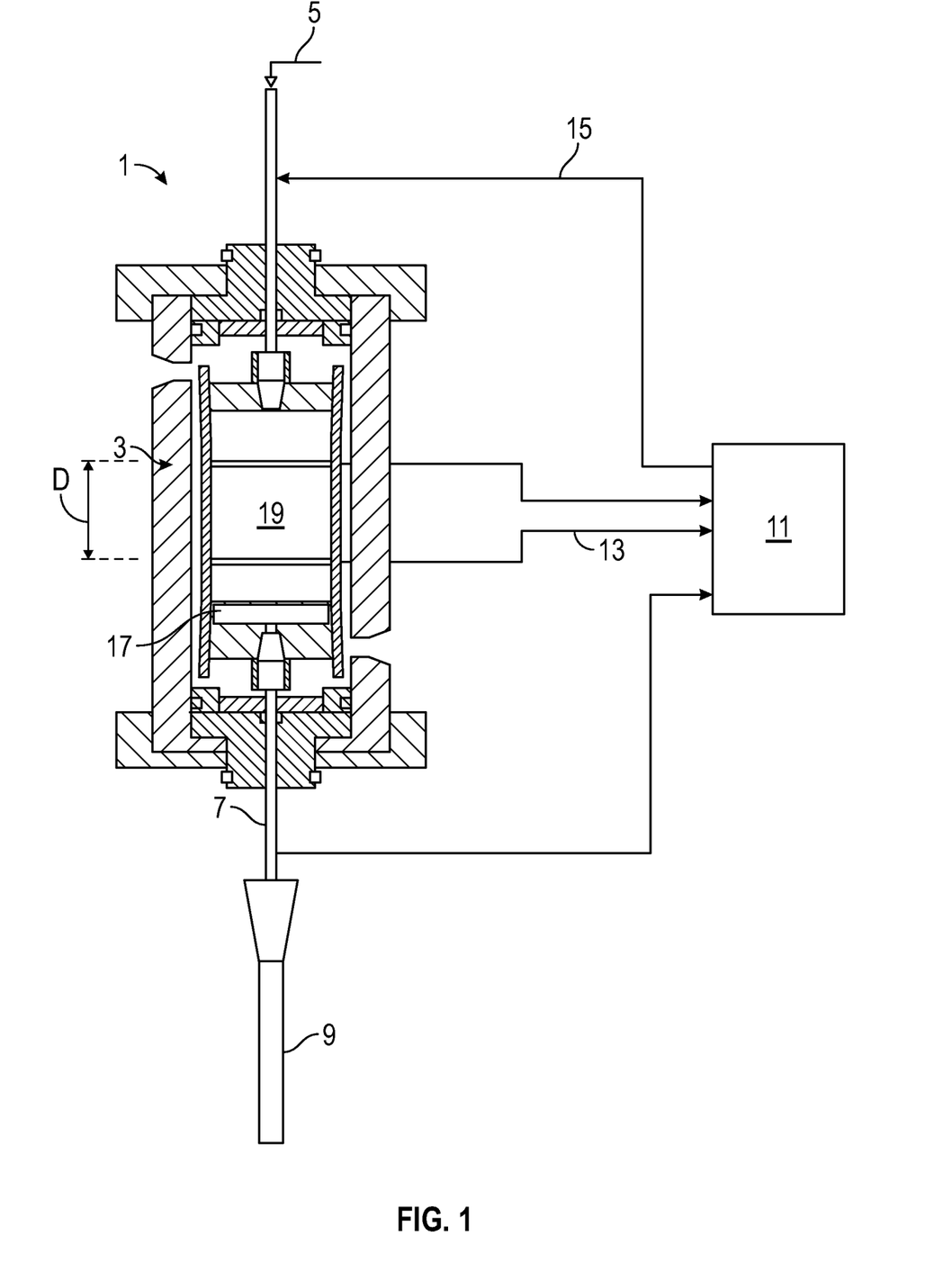
FIG. 1 shows a cross-sectional view of an apparatus for determining the electrical conductivity of a core sample.
Figure 2A:
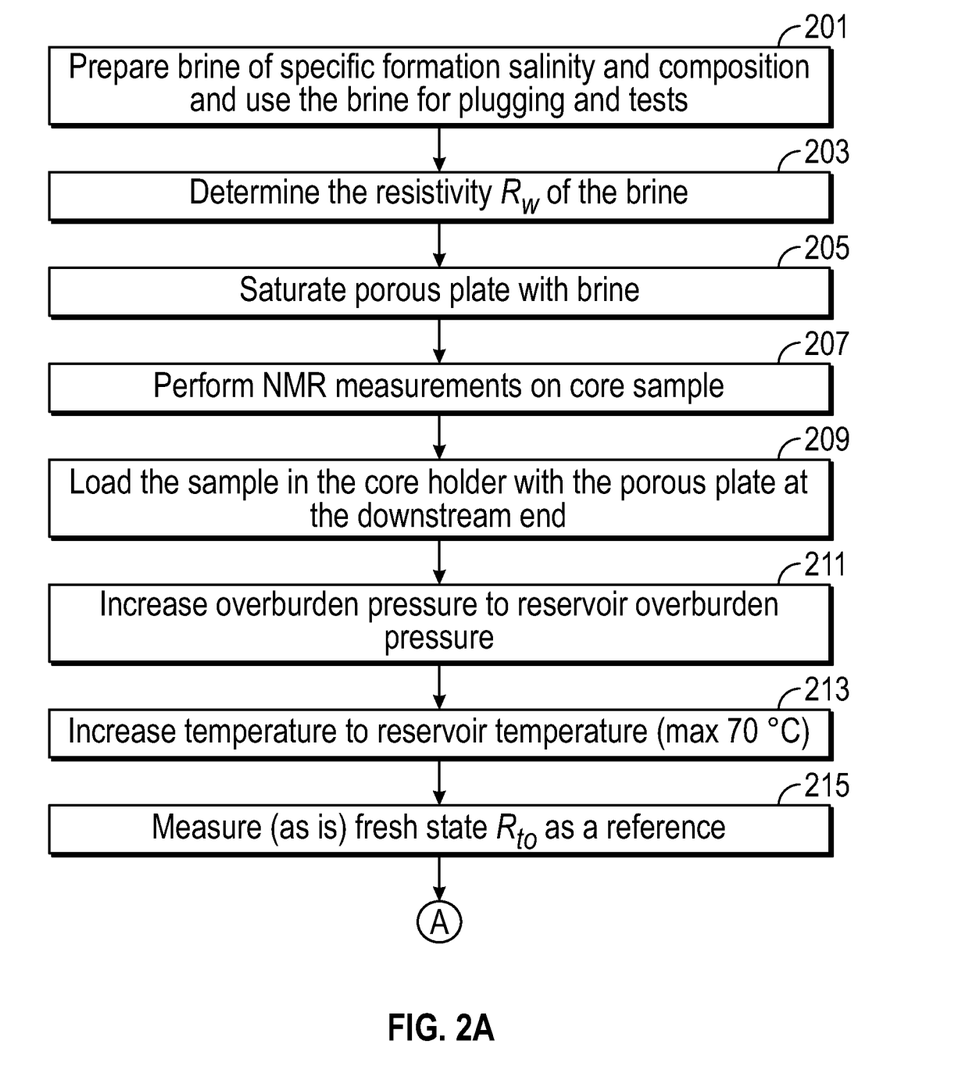
FIG. 2A shows a flowchart illustrating the steps 201-215 of the method for determining the cementation and saturation exponent m, n of a core sample.
Figure 2B:
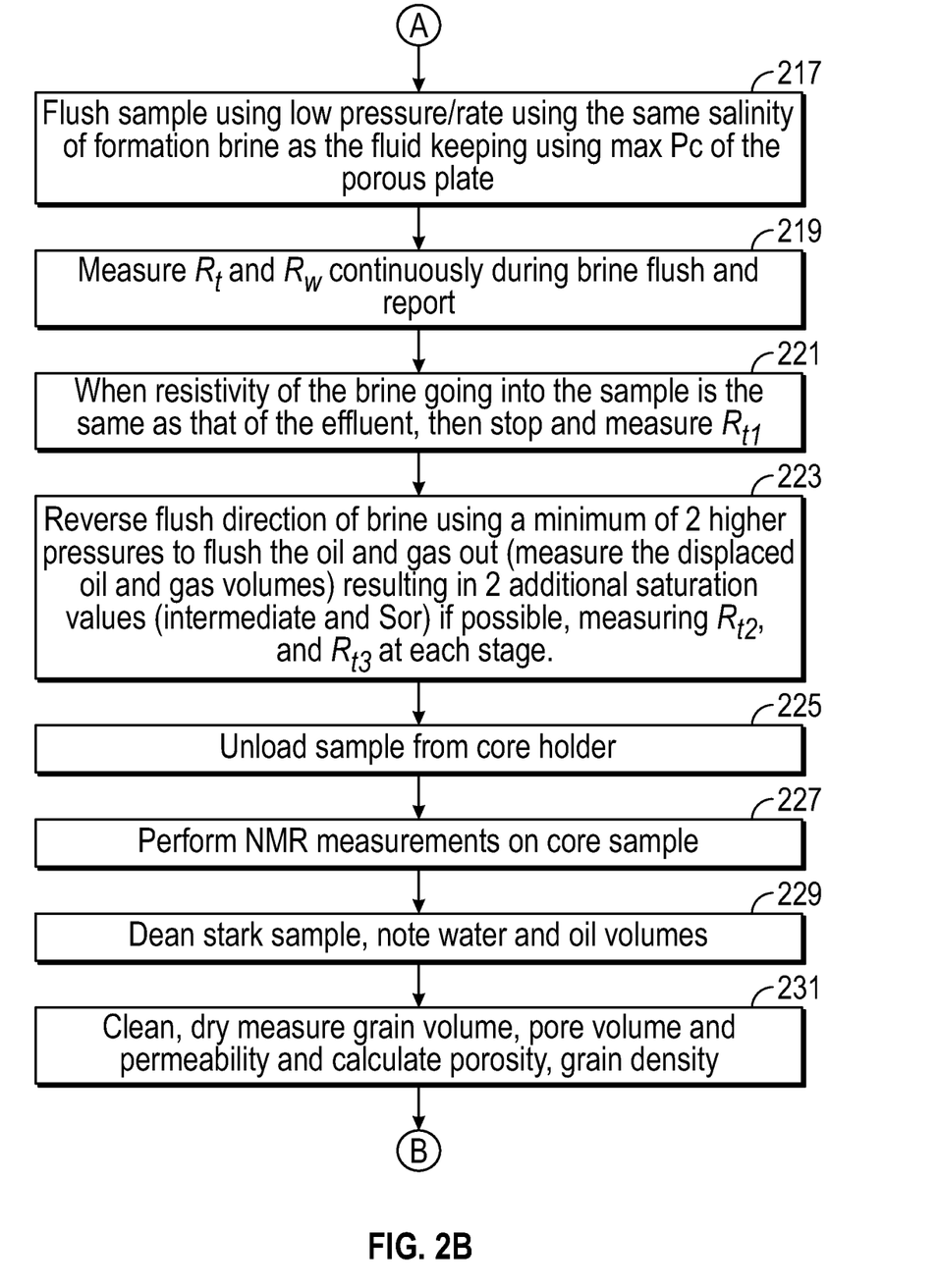
FIG. 2B shows a flowchart illustrating the steps 217-231 of the method for determining the cementation and saturation exponent m, n of a core sample.
Figure 2C:
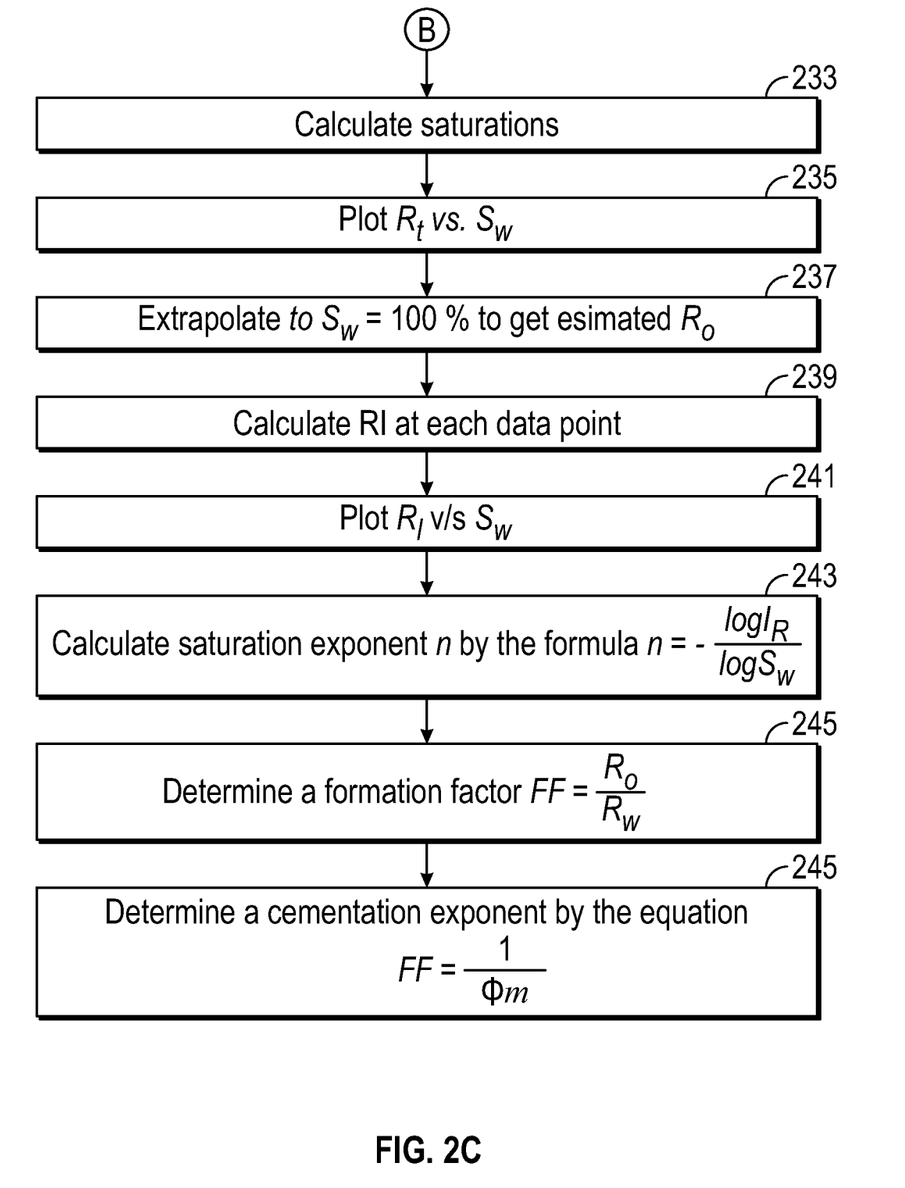
FIG. 2C shows a flowchart illustrating the steps 233-245 of the method for determining the cementation and saturation exponent m, n of a core sample.

FIG. 1 shows a cross-sectional view of an apparatus for determining the electrical conductivity of a core sample, and FIGS. 2A-2C show a flowchart illustrating the steps of the method for determining the cementation and saturation exponent m, n of a core sample. The following description refers to the FIGS. 1, 2A-2C simultaneously.

A native- or fresh state core sample 19 should be used for the method of determining the electrical properties of the core sample 19, unless it is known that the formation is strongly water-wet. A native- or fresh state core sample 19 may exhibit the original wettability of the formation under consideration. If a clean core sample 19 is used for the method of determining the electrical properties of the core sample 19 and the core sample 19 was initially oil-wet, the clean core sample test may give false results.

While its described in the literature that all clean minerals of a core sample are wet, the wettability will depend on the affinity of the core sample 19 to polar compounds. Carbonates have more affinity to polar compounds than sandstones.

In one or more embodiments, the polar compounds are dissolved in oil above a certain pressure and temperature and may fall out at lower fluid pressures. Once the polar compounds begin to flocculate in the oil, they settle and eventually pass through the water film and adhere themselves to the core sample 19 changing its wettability. This change becomes more important in case the content of the asphaltenes and waxes is more than 2% of the oil. Therefore, in case polar compounds are deposited in the core sample 19, the core sample 19 will show a high degree of oil-wetness.

At step 201, a simulated brine is prepared that simulates the liquid in the reservoir rock. The simulated brine comprises the ionic composition of the brine from the formation (formation brine). The formation brine is reconstituted by mixing various salts together in distilled water. The brine is used for plugging and tests as described below.

The simulated Brine flows through a rotating swivel and onto the core sample. A cylindrical coring bit then cuts the core sample and takes a small cylindrical sub core sample of the core sample. The simulated brine is used as a lubricant and also as a medium to flush the debris out from the surface of the drill bit. The horizontal plug is 1.5" in diameter and is trimmed to achieve a maximum length of 3.25".

At step 203, the resistivity $R_w$ of the brine is determined. The resistivity of the brine is measured by a conductivity meter comprising two electrodes disposed distantly from each other. The electrodes are immersed into the brine and the conductivity meter applies an alternating voltage to the electrodes to avoid electrolysis at the electrodes with the brine. The conductivity meter determines the resistance of the brine between the electrodes and calculates the resistivity $R_w$ of the brine from the resistance of the brine between the electrodes.

At step 205, the porous plate is saturated with the brine. The porous plate is kept in a chamber under high vacuum for 6-8 hours. The brine is then introduced into the chamber to allow for the chamber and the empty pores in the porous plate to be saturated with the brine. Once the chamber is filled with the brine, the chamber is pressurized to 2000 psig to force the brine into the smaller pore spaces.

At step 207, the total liquid filled volume within the pore space of the core sample and the content of oil and water volumes in the core sample are determined by nuclear magnetic resonance (NMR) spectroscopy. NMR spectroscopy provides a method to cross check the measurement of the saturation of the core sample.

When a core sample is placed in a magnetic field and activated with a quick pulse of radio frequency (RF), NMR signals are generated from liquids such as brine or oil. An NMR signal is formed instantaneously after the pulse, which then dies away with a characteristic decay rate or relaxation time known as T2. The amplitude of the signal immediately after the pulse indicates the total amount of fluid present. T2 of the signal provides important information about the physical environment of the liquids.

In pores filled with a single fluid, there are two key components to the NMR signal, one signal is generated from the fluid far from the pore walls and another close to the pore walls. The nature of NMR signals in fluids far from the pore walls is similar to those from bulk fluids having comparatively long relaxation times, whereas fluids close to the pore walls undergo a process of adsorption and desorption with the pore walls which has the effect of drastically reducing their NMR relaxation times.

In large pores, the dominant effect is from the bulk fluids, so larger pores have longer NMR relaxation times. In smaller pores, the surface-to-volume ratio is much higher, hence the fluids near the pore wall dominate the NMR signal, and smaller pores display overall shorter NMR relaxation times.

NMR is commonly used to determine effective porosity and pore size distributions but it is important to note that NMR can also measure fluid mobility parameters such as bound volume irreducible (BVI), free fluid index (FFI), clay bound water (CBW) fluid saturation, diffusion coefficient, permeability models, wetting characteristics and oil viscosity.

In this process, NMR is used to predict total fluid volumes. Industry accepted procedures can be used to predict other parameters if NMR tests are carried out on the same core sample in clean state and/or restored state conditions.

FIG. 1 shows a cross-sectional view of an apparatus 1 for determining the electrical conductivity of a core sample. The apparatus comprises a core holder 3 which allows for applying confining stress on a core sample 19 equivalent to the reservoir overburden pressure and temperature (max. 75° C.).

At step 209 the core sample is inserted in a rubber sleeve 21. A hydrophilic porous plate 17 is placed at the bottom end of the core sample 19. Silver paint is used to improve the conductivity between the electrodes and the core sample. A porous silver screen or filter can be placed in between the core sample 19 and the porous plate 17 to ensure the conductivity and the capillary continuity between the core sample 19 and the porous plate 17. An outlet end stem 7 is placed at the bottom of the porous plate 17. Some brine is poured at the top end of the core sample 19 and inserted at an inlet end stem 5 at the top end of the core sample 19 ensuring that the top end stem is filled with brine. This setup allows for passage of fluids through the core sample 19 when it is held under reservoir overburden stress.

The brine in the core sample 19 can be easily replaced with a brine of a composition matching that of the formation by flushing the core sample with brine of known salinity without displacing the oil. This is achieved by using a water wet porous plate with maximum air-brine capillary pressure Pc of 1000 psig or more and flushing the core sample with brine. This will make only brine flow through the core sample and the porous plate. If any, the oil and gas is left behind the capillary end effect. For a water wet core sample, the brine is transferred to the porous plate 17 and a uniform brine distribution is maintained in the core sample 19 with up to 1000 psig of capillary pressure.

Once the core sample 19 is placed in the core holder 3 and the reservoir overburden stress is applied, the core sample 19 and the porous plate 17 are in capillary contact. The brine flowing from the inlet 5 into the apparatus 1 flows through the core sample 19 and then through the porous plate 17 to the outlet 7.

At step 211, the overburden pressure is increased to reservoir overburden pressure. The overburden pressure simulates the weight of the overlying reservoir rock. The core sample 19 is always kept under conditions of overburden pressure to represent actual pore volumes and pore throat sizes of the reservoir rock. The probability of the core sample breaking is very low.

At step 213, the temperature is now increased in steps to reservoir temperature (max. 70° C.). To achieve this, the core holder may be placed in a jacket or in a temperature controlled oven. The core sample 19 is now ready for initial measurement of the resistivity.

At step 215, the (as is) resistivity of the core sample $R_{t0}$ is measured. This value is to be kept for reference only and is useful in determining invasion of drilling fluid filtrate. Once the core sample 19 is disposed inside the core holder 3, an Inductance-Capacitance-Resistance (LCR) meter 11 with four-terminal sensing technique is connected to the apparatus 1. In one or more embodiments, the LCR meter is a stand-alone instrument. In other embodiments, the LCR meter is implemented in the apparatus 1. The LCR meter comprises a pair of voltage electrodes 13 and a pair of current electrodes 15. The voltage electrodes 13 are disposed near a center of the core sample 19 and measure the voltage across the core sample 19. The current electrodes 15 are placed near the ends of the core sample 19 and measure the current flowing through the core sample 19. In one or more embodiments, each of the pair of the voltage electrodes 13 are disposed on the core sample 19 at distance D of around one inch from each other.

At step 217, the core sample is flushed with a brine of same salinity than that of the porous plate at a low pressure (minimum required to flush the core sample) and flush rate (0.5-1.0 cc/min), while not exceeding the maximum capillary pressure $P_c$ on the porous plate. The brine in the core sample is expelled through the porous plate 17 through the outlet end 7 leaving the oil and gas behind.

The effluent brine is periodically measured for resistivity and the brine in the core sample is considered replaced when the resistivity of the brine flowing into the core sample is the same as the resistivity of the brine flowing out of the core sample.

In one or more embodiments, the four electrode system is configured to provide a comparison between two sets of measurements. One set is obtained along the entire length of the core sample and the other set is obtained along the central length of the core sample of one inch. If the saturation distribution in the core sample is uniform, and the core sample is homogenous, very little difference can be measured in the resistivity between the central and the outer electrodes. In highly oil wet systems, a difference may be observed, especially at higher oil saturations.

If the core sample 19 is water wet, when flushed with the brine, oil may be displaced and accumulated at the outlet end of the core sample 19 (above the porous plate 17). The four-terminal sensing technique is able to detect this effect.

The four-terminal sensing technique provides a comparison between two sets of measurements: along the entire length of the core sample, along the distance D. If the saturation is distributed uniformly in the core sample, very little difference may be observable in the resistivity measurement between the voltage electrodes and the current electrodes. The difference may be observable in highly oil wet core samples, especially at higher oil saturations. Once the fluid in the core sample is replaced with brine, the flow pressures of the brine in the core sample is reduced. This allows the fluids in the core sample to redistribute capillary.

Figure 3:
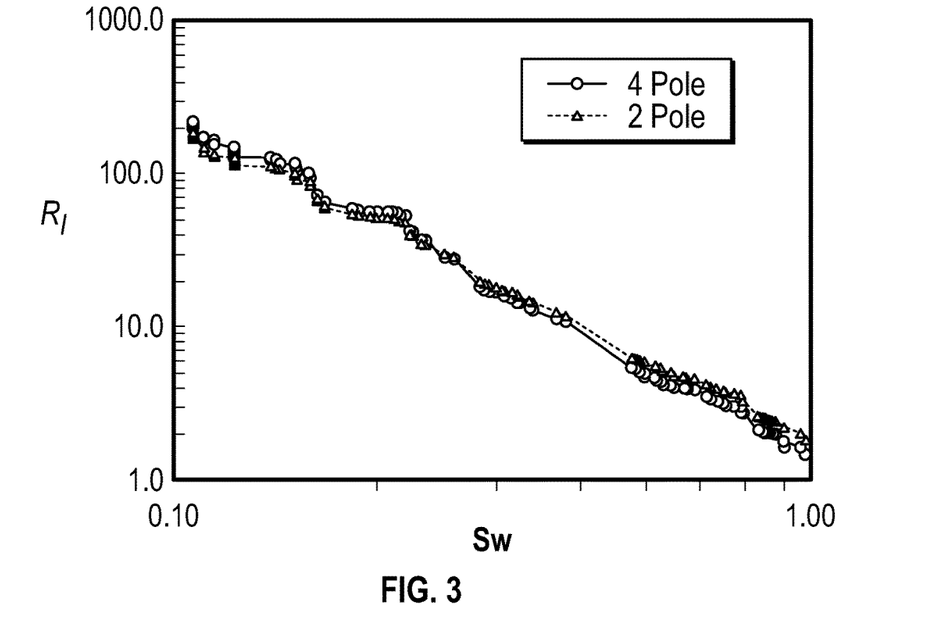
FIG. 3 shows a plot of the resistivity index $R_I$ of a core sample as a function of the saturation $S_w$ in the core sample.

FIG. 3 shows an example plot of measurements of the resistivity $R_t$ of a core sample as a function of the saturation $S_w$ in the core sample using 4 electrode and a 2 electrode methods. If the capillary end effect is negligible and there is uniform saturation distribution, the 2 sets of data should match.

At step 219, the true resistivity $R_t$ of the core sample and the resistivity $R_w$ of the brine are determined continuously during the flush at conditions of overburden and temperature of a reservoir rock.

At step 221, a first true resistivity $R_{t1}$ of the core sample at a first saturation $S_{w1}$ is determined, when resistivity $R_w$ of the brine going into the core sample is the same as the resistivity $R_w$ of the effluent brine.

At step 223, the flush direction of the brine is reversed using a minimum of two higher pressures to flush the oil and gas out of the core sample. At the same time the displaced oil and gas volumes are measured. This results in two additional saturations $S_{w1}$, $S_{w2}$ (an intermediate oil saturation and a final or residual oil saturation), and two additional resistivities $R_{t2}$, $R_{t3}$ at each of the two additional saturations $S_{w1}$, $S_{w2}$.

At step 225, the core sample 19 is unloaded from the core holder 1.

At step 227, the total liquid filled volume within the pore space (saturation) of the core sample and the difference between oil and water volumes in the core sample are determined by NMR.

At step 229, the saturation in the core sample is determined by obtaining a Dean-Stark-sample from Dean-Stark extraction. Water and oil volumes are noted. Dean-Stark extraction measures the saturation in the core sample by distillation extraction. The water in the core sample is vaporized by a boiling solvent, then the vaporized water is condensed and collected in a calibrated trap. This gives the volume of the fluid in the core sample. The solvent is also condensed, then flows back over the core sample and extracts the oil in the core sample. The saturation is calculated from the volumes of the extracted fluid and oil.

At step 231, the core sample 19 is cleaned, dried, and grain volume and pore volume and permeability are measured. The porosity $\phi$ and grain density of the core sample are calculated.

At step 233, saturations are calculated by using the volumes of oil, water and gas recovered and the measured pore volume.

At step 235, the true resistivity $R_t$ of a core sample versus the saturation $S_w$ in the core sample is plotted. The plot is shown in FIG. 3.

At step 237, a linear function $R_t=f(S_w)$ describing the dependency of the true resistivity $R_t$ and the saturation $S_w$ of the brine in the core sample is determined. The function $R_t=f(S_w)$ is shown in FIG. 4.

Figure 4:
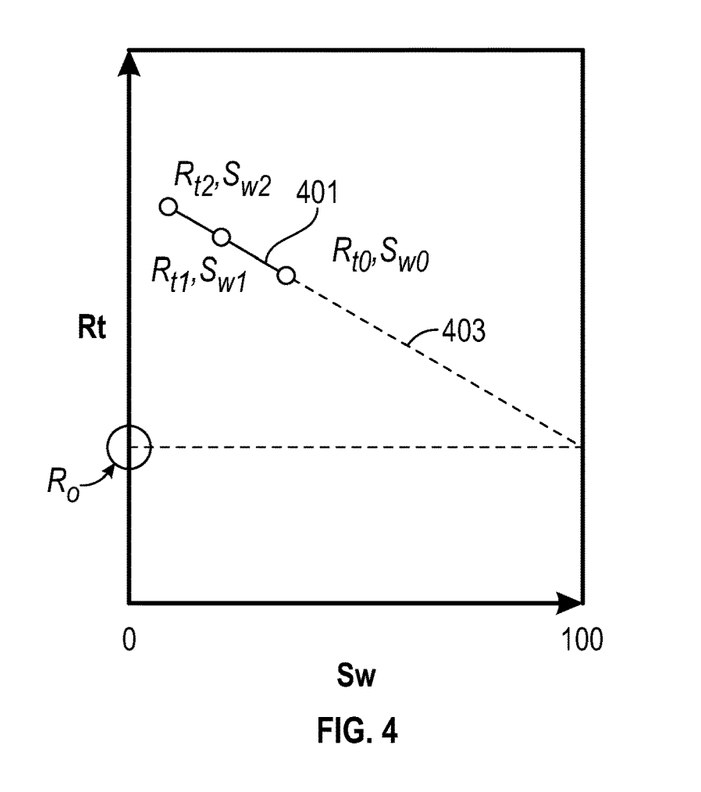
FIG. 4 shows a plot of a linear function $R_t = f(S_w)$ describing the dependency of the true resistivity $R_t$ of a core sample and the saturation $S_w$ in the core sample.
Figure 5:
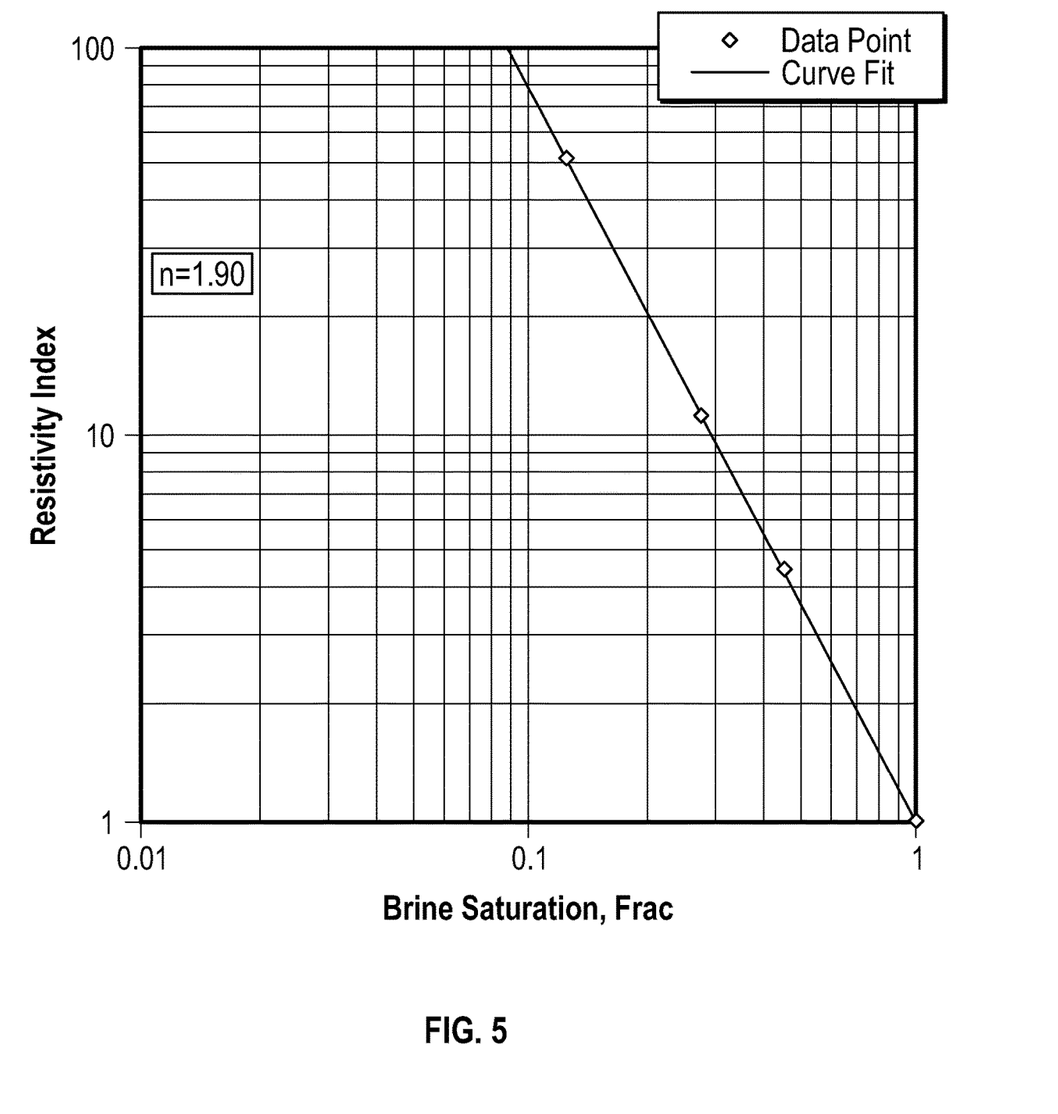
FIG. 5 shows another plot of the resistivity index $R_I$ vs. the saturation $S_w$ in the core sample.

At step 239, the linear function $R_t=f(S_w)$ is extrapolated to full saturation of the core sample at $S_w=100\%$ to determine the resistivity $R_o$ of the fully saturated core sample as shown in FIG. 4.

At step 241, a resistivity index $$I_R = \frac{R_t}{R_o} = S_w^{-n}$$

is determined at each saturation $S_w$. The resistivity index $I_R$ is the ratio of the true resistivity $R_t$ of the core sample to resistivity $R_o$ of the fully saturated core sample.

At step 243, a saturation exponent n is determined by a linear best fit line equation by plotting $I_R$ vs. Saturation on a log-log scale.

FIG. 4 shows a plot of the linear function $R_t=f(S_w)$ describing the dependency of the true resistivity $R_t$ of the core sample and the saturation $S_w$ in the core sample. The function $R_t=f(S_w)$ is illustrated as solid line 401. The x-axis shows the true resistivity $R_t$ of the core sample and the y-axis shows the saturation $S_w$ in the core sample. In some embodiments, the function $R_t=f(S_w)$ is determined from three measuring points: the initial true resistivity $R_{t0}$ at the initial saturation $S_{w0}$ ($R_{t0},S_{w0}$), the first true resistivity $R_{t1}$ at the first saturation $S_{w1}$ ($R_{t1},S_{w1}$), and the second true resistivity $R_{t2}$ of the core sample at the second saturation $S_{w2}$ in the core sample ($R_{t2},S_{w2}$). In other embodiments, the function $R_t=f(S_w)$ is determined from two measuring points only: the initial true resistivity $R_{t0}$ at the initial saturation $S_{w0}$ ($R_{t0},S_{w0}$), and the first true resistivity $R_{t1}$ at the first saturation $S_{w1}$ ($R_{t1},S_{w1}$) or the first true resistivity $R_{t1}$ at the first saturation $S_{w1}$ ($R_{t1},S_{w1}$), and the second true resistivity $R_{t2}$ of the core sample at the second saturation $S_{w2}$ in the core sample ($R_{t2},S_{w2}$).

In one or more embodiments, the function $R_t=f(S_w)$ describes a linear dependency between the true resistivity $R_t$ of the core sample and the saturation $S_w$ in the core sample. Therefore, the function $R_t=f(S_w)$ is determined by interpolation, i. e. linear interpolation, i. e. linear regression.

Once the function $R_t=f(S_w)$ is determined, the resistivity $R_o$ of the fully saturated core sample can be determined by estimation.

In one or more embodiments, the resistivity $R_0$ of the fully saturated core sample is determined by extrapolation of the function $R_t=f(S_w)$ to full saturation of the core sample at $S_w=100\%$. In case the function $R_t=f(S_w)$ is a linear function, the resistivity $R_0$ of the fully saturated core sample is determined by linear extrapolation of the function $R_t=f(S_w)$ to full saturation of the core sample at $S_w=100\%$. The extrapolation of the function $R_t=f(S_w)$ is illustrated as a dashed line 403 in FIG. 4. The extrapolation 403 of the linear function $R_t=f(S_w)$ to full saturation of the core sample at $S_w=100\%$ determines the resistivity $R_o$ of the fully saturated core sample.

The saturation exponent n depends on the presence of non-conductive fluid in the pore space of the core sample. Water-wet core samples will maintain a continuous film along the pore walls which makes the core sample conductive, hence have a smaller n value. Oil-wet core samples may have discontinuous droplets of water within the pore space which makes the core sample less conductive and hence have a larger n value.

In water-wet rocks n is constant for different saturations $S_w$. A typical theoretical value used for quick calculations for the saturation exponent n is 2. Knowing the correct value of the saturation exponent is extremely useful in calibrating downhole electrical resistivity logs to determine the oil and water saturations of the formation.

At step 245, a formation factor $$FF = \frac{R_o}{R_w}$$

is determined.

At step 247, the cementation exponent m is determined by the equation $$m = -\frac{\log FF}{\log \Phi}$$

which follows from the equation $$FF = \frac{1}{\Phi^m}.$$

The cementation exponent models how much the pore network increases the resistivity, as the rock itself is assumed to be non-conductive. If the pore network were to be modelled as a set of parallel capillary tubes, a cross-section area average of the rock's resistivity would yield porosity dependence equivalent to a cementation exponent of 1. However, the tortuosity of the rock increases this to a higher number than 1. This relates the cementation exponent to the permeability of the rock, increasing permeability decreases the cementation exponent.

The exponent m has been observed near 1.3 for unconsolidated sands, and is believed to increase with cementation. Common values for this cementation exponent for consolidated sandstones are 1.8<m<2.0. In carbonate rocks, the cementation exponent shows higher variance due to strong diagenetic affinity and complex pore structures. Values between 1.7 and 4.1 have been observed.

The cementation exponent is assumed not to be dependent on temperature.

Knowing the correct value of the cementation exponent is extremely useful in calibrating downhole electrical resistivity logs to determine porosity of the formation.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed:

1. A method comprising:
preparing a brine having a resistivity $R_w$,
flushing, using an apparatus comprising a core holder and a conductivity meter, a core sample with the brine, wherein the core sample is disposed in the core holder;
determining, using the conductivity meter comprising a first electrode and a second electrode, a first true resistivity $R_{t1}$ at a first saturation $S_{w1}$ of the core sample, once a resistivity $R_w$ of the brine going into the core sample is the same as a resistivity $R_w$ of the brine going out of the core sample;
determining, using the conductivity meter, a function $R_t=f(S_w)$ describing a dependency of a true resistivity $R_t$ of the core sample and a saturation $S_w$ in the core sample, based on an initial saturation $S_{w0}$, initial true resistivity $R_{t0}$, the first true resistivity $R_{t1}$, and the first saturation $S_{w1}$, a second true resistivity $R_{t2}$, and a first saturation $S_{w2}$;
determining, using the apparatus, a resistivity $R_o$ of a fully saturated core sample by estimating a function $R_t=f(S_w)$ to full saturation of the core sample at $S_w=100\%$;
determining, using the apparatus, a resistivity index $$I_R = \frac{R_t}{R_o} \text{ at the } S_{w0}, S_{w1}, S_{w2};$$

determining, using the apparatus, a saturation exponent n using linear regression of log-log plot of $I_R$ vs. $S_w$; and
determining, using the apparatus, one or more electrical properties of the core sample based on the saturation exponent.

2. The method according to claim 1, further comprising: determining a formation factor $$FF = \frac{R_0}{R_w},$$

and determining a cementation exponent $$m = -\frac{\log FF}{\log \Phi}.$$

3. The method according to claim 1, wherein the core sample is brought in capillary contact with a porous plate before flushing the core sample with the brine.

4. The method according to claim 3, wherein the porous plate is saturated with the brine before flushing the core sample with the brine.

5. The method according to claim 3, wherein the core sample and the porous plate are flushed with the brine.

6. The method according to claim 1, wherein the core sample is flushed with the brine at a low pressure that is minimum required for the brine to flow through the core sample.

7. The method according to claim 1, wherein the core sample is flushed with the brine at a low flush rate of 0.5-1 cc/min.

8. The method according to claim 1, wherein the initial true resistivity $R_{t0}$ of the core sample is measured at conditions of overburden and temperature of a reservoir rock.

9. The method according to claim 8, wherein a flush direction of the brine is reversed before determining the second true resistivity $R_{t1}$ and a second saturation $S_{w1}$ of the core sample.

10. The method according to claim 9, wherein the flush direction of the brine is reversed by two higher pressures or flow rates.

11. The method according to claim 1, wherein a second true resistivity $R_{t1}$ of the core sample at a second saturation $S_{w1}$ in the core sample are determined and used for determining the function $R_t=f(S_w)$.

12. The method according to claim 1, wherein a third true resistivity $R_{t2}$ of the core sample at a second saturation $S_{w2}$ in the core sample are determined and used for determining the function $R_t=f(S_w)$.

13. The method according to claim 1, wherein a second resistivity index $$I_{R2} = \frac{R_{t2}}{R_o}$$

is determined at a second saturation $S_{W2}$ and a third resistivity index $$I_{R2} = \frac{R_{t2}}{R_o}$$

is used to plot data on a log-log scale and determine the saturation exponent n by linear regression.

14. The method according to claim 1, wherein the function $R_t=f(S_w)$ is determined by interpolation.

15. The method according to claim 1, wherein the function $R_t=f(S_w)$ is determined by linear interpolation.

16. The method according to claim 1, wherein the function $R_t=f(S_w)$ is determined by linear regression.

17. The method according to claim 1, wherein the true resistivity $R_t$ of the core sample is continuously monitored during flushing of the brine.

18. The method according to claim 1, wherein the resistivity $R_w$ of the brine is continuously monitored during flushing of the brine.

19. The method according to claim 1, wherein the resistivity $R_o$ of the fully saturated core sample is determined by extrapolation of the function $R_t=f(S_w)$ to full saturation of the core sample at $S_w=100\%$.

20. The method according to claim 1, wherein the resistivity $R_o$ of the fully saturated core sample is determined by linear extrapolation of the function $R_t=f(S_w)$ to full saturation of the core sample at $S_w=100\%$.

* * * * *